United States Patent
Gehle

(10) Patent No.: US 9,655,635 B2
(45) Date of Patent: May 23, 2017

(54) GUIDEWIRE RETRIEVAL SYSTEM

(71) Applicant: Covidien LP, Mansfield, MA (US)

(72) Inventor: Kevin Gehle, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 112 days.

(21) Appl. No.: 14/667,909

(22) Filed: Mar. 25, 2015

(65) Prior Publication Data

US 2016/0278796 A1   Sep. 29, 2016

(51) Int. Cl.
 *A61B 17/22* (2006.01)
 *A61B 17/221* (2006.01)
 *A61B 17/50* (2006.01)
 *A61M 25/09* (2006.01)

(52) U.S. Cl.
 CPC ............ *A61B 17/221* (2013.01); *A61B 17/50* (2013.01); *A61M 25/09041* (2013.01); *A61B 2017/22001* (2013.01); *A61B 2017/2215* (2013.01); *A61B 2017/22035* (2013.01); *A61B 2017/22094* (2013.01); *A61M 2025/09116* (2013.01); *A61M 2025/09125* (2013.01)

(58) Field of Classification Search
 CPC . A61B 17/22; A61B 17/22031; A61B 17/221; A61B 17/32056; A61B 17/50; A61B 2017/22035; A61B 2017/22072; A61B 2017/22078; A61B 2017/22094; A61B 2017/2212; A61B 2017/2215; A61B 2017/2217; A61M 25/09041
 See application file for complete search history.

(56) References Cited

U.S. PATENT DOCUMENTS

| | | | |
|---|---|---|---|
| 4,706,671 A | 11/1987 | Weinrib | |
| 5,464,408 A * | 11/1995 | Duc | A61B 17/29 606/108 |
| 6,187,016 B1 * | 2/2001 | Hedges | A61B 17/221 606/108 |
| 7,753,918 B2 * | 7/2010 | Hartley | A61B 17/221 606/108 |
| 7,918,859 B2 | 4/2011 | Katoh et al. | |
| 8,167,903 B2 * | 5/2012 | Hardert | A61B 17/221 606/127 |
| 2010/0114135 A1 | 5/2010 | Wilson et al. | |
| 2013/0317485 A1 | 11/2013 | Lupton | |
| 2014/0025086 A1 | 1/2014 | Rottenberg et al. | |

FOREIGN PATENT DOCUMENTS

| | | |
|---|---|---|
| WO | 9727808 A1 | 8/1997 |
| WO | 0020064 A1 | 4/2000 |
| WO | 0202162 A2 | 1/2002 |

OTHER PUBLICATIONS

International Search Report and Written Opinion for Application No. PCT/US2016/023473, Jun. 9, 2016, 13 pages.

* cited by examiner

*Primary Examiner* — Ryan J Severson

(57) ABSTRACT

A guidewire retrieval system generally comprises a guidewire capture device. The guidewire capture device includes a hoop member defining a hoop passage for receiving the guidewire therein, and a hook member extending inwardly from the hoop member toward the axis of the guidewire capture device. The hook member is configured to capture the guidewire received in the hoop passage as the guidewire capture device is rotated about its axis.

19 Claims, 15 Drawing Sheets

GUIDEWIRE RETRIEVAL SYSTEM

FIELD OF THE DISCLOSURE

The present invention generally relates to a guidewire retrieval system for retrieving a retrograde guidewire from a body lumen.

BACKGROUND OF THE DISCLOSURE

In some medical procedures, it may be necessary to retrieve a guidewire disposed within a body lumen. In particular, in some cases a guidewire may need to be advanced through a body lumen in a direction that is opposite that of the advancement of the medical device used with the guidewire. Introducing the guidewire in such a fashion is a retrograde procedure. A guidewire may be introduced in a retrograde procedure when attempting to re-vascularize a chronic total occlusion (CTO) of an arterial vessel. In such a procedure, it may be difficult to penetrate a proximal cap of the CTO with the guidewire. Accordingly, a tip portion of the guidewire is introduced at distal location relative to the CTO so that the tip portion of the guidewire can penetrate a softer distal cap of the CTO. After passing through the CTO from a distal location, the leading or distal end of the guidewire must be retrieved and passed outside the body so that the desired medical device can be received on the guidewire and delivered to the treatment site.

SUMMARY OF THE DISCLOSURE

In one aspect, a guidewire retrieval system for use in retrieving a guidewire from a body lumen generally comprises a guidewire capture device. The guidewire capture system includes a hoop member defining a hoop passage for receiving the guidewire therein, and a hook member extending inwardly from the hoop member toward the axis of the guidewire capture device. The hook member is configured to capture the guidewire received in the hoop passage as the guidewire capture device is rotated about its axis. A method of using the guidewire retrieval system to retrieve a guidewire from a body lumen is also disclosed.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
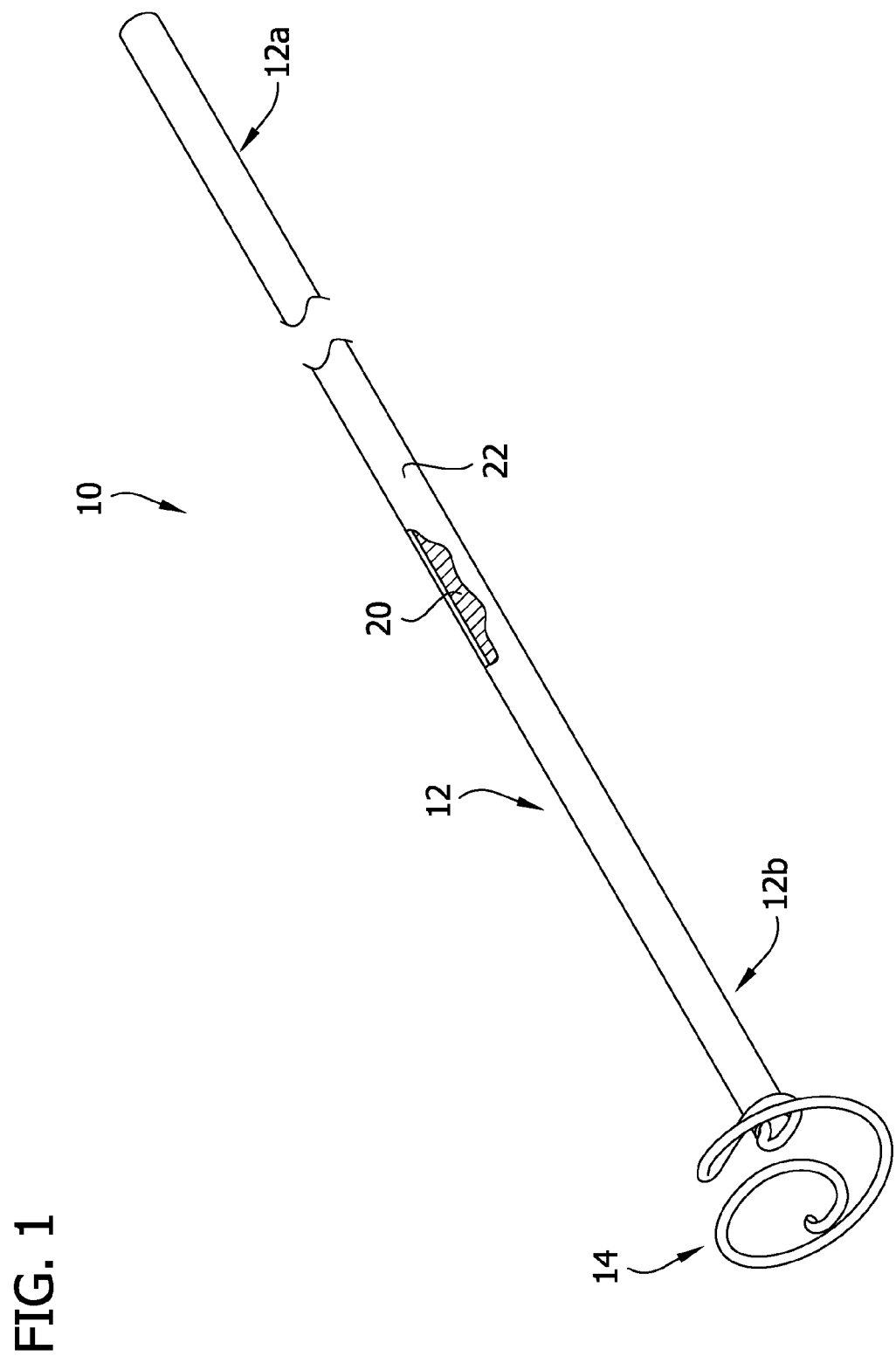
FIG. 1 is a fragmentary perspective of one embodiment of a guidewire retrieval system.
Figure 2:
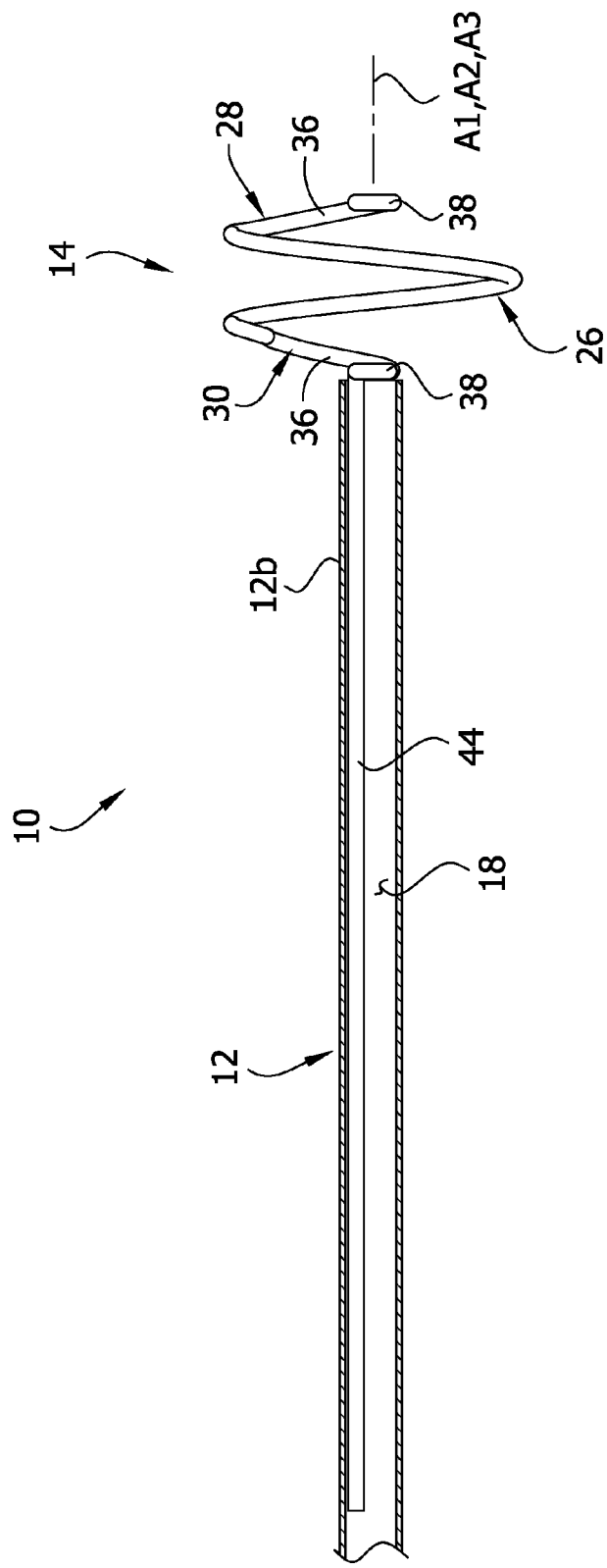
FIG. 2 is an enlarged, fragmentary longitudinal section of the guidewire retrieval system including a distal end thereof.

Referring to FIG. 1, a guidewire retrieval system for retrieving a guidewire disposed within a body lumen is generally indicated at reference numeral 10. As explained below, it is envisioned that the guidewire retrieval system 10 will be used during a medical procedure to facilitate retrieval of a retrograde guidewire that is introduced into the body lumen via a retrograde approach. The illustrated guidewire retrieval system 10 comprises a retrieval catheter, generally indicated at reference numeral 12, and a guidewire capture device, generally indicated at reference numeral 14. It is understood that the retrieval catheter 12 may be omitted from the guidewire retrieval system 10 without departing from the scope of the present invention. Referring to FIG. 2, the retrieval catheter 12 comprises a tubular body defining a guidewire retrieval lumen 18 having a longitudinal axis A1 extending lengthwise of and generally coaxial with the retrieval catheter and configured to receive a distal end portion of a retrograde guidewire therein. The retrieval catheter 12 has proximal and distal end portions 12a, 12b, and a length extending between the proximal and distal end portions. As explained in more detail below, in the illustrated embodiment, the guidewire capture device 14 is disposed at the distal end portion 12b of the retrieval catheter 12. The retrieval catheter 12 has a suitable outer dimension for insertion into a desired body lumen, such as a peripheral artery of the leg, other blood vessels, or other body lumens. The retrieval catheter 12 may be generally flexible to allow tracking through a tortious body lumen. The retrieval catheter 12 may also comprise a polymeric material 22 (FIG. 1), such as, but not limited to, thermoplastic elastomer, nylon, polyurethane, polyethylene terephthalate, and blends thereof, disposed over a torque tube 20.

Figure 3:
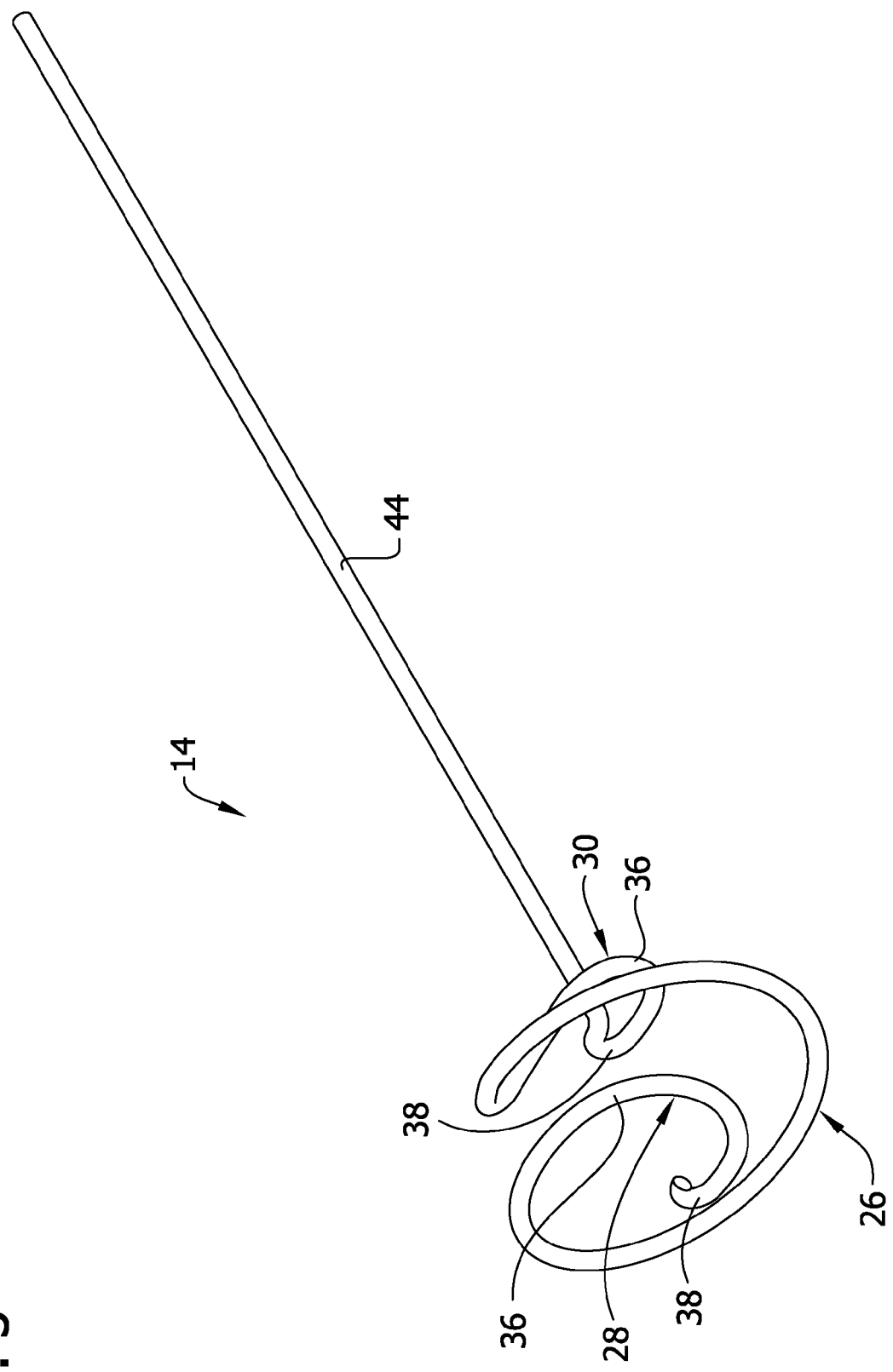
FIG. 3 is an enlarged perspective of a guidewire capture device of the guidewire retrieval system.

The guidewire capture device 14 is configured to capture the guidewire to facilitate alignment of the guidewire with the guidewire retrieval lumen 18 of the retrieval catheter 12 and insertion of the guidewire into the guidewire retrieval lumen. Referring to FIGS. 2 and 3, the guidewire capture device 14 comprises a hoop member, generally indicated at 26, and first and second hook members, generally indicated at 28, 30, respectively, connected to the hoop member. In other embodiments, the guidewire capture device 14 may include one hook member or more than two hook members within the scope of the present invention. The guidewire capture device 14 is expandable from a collapsed configuration (FIG. 5) to an expanded configuration, as illustrated. In one example, the guidewire capture device 14 may be formed from a shape memory material, such as nitinol, such that the guidewire capture device assumes the expanded configuration when delivered into the body lumen. In this example, the temperature of the body causes the guidewire capture device 14 to assume that expanded configuration. In another embodiment, the guidewire capture device 14 may be elastically deformable such that when disposed inside an introducer sheath or other catheter, the guidewire capture device is in the collapsed configuration, and when the guidewire capture device is outside the introducer sheath, the guidewire capture device rebounds to the expanded configuration. In its expanded configuration, the guidewire capture device 14 has an axis A2 extending outward from the distal end portion 12b of the retrieval catheter 12 that is generally coaxial with the axis A1 of the guidewire retrieval lumen 18 and the retrieval catheter.

Figure 4:
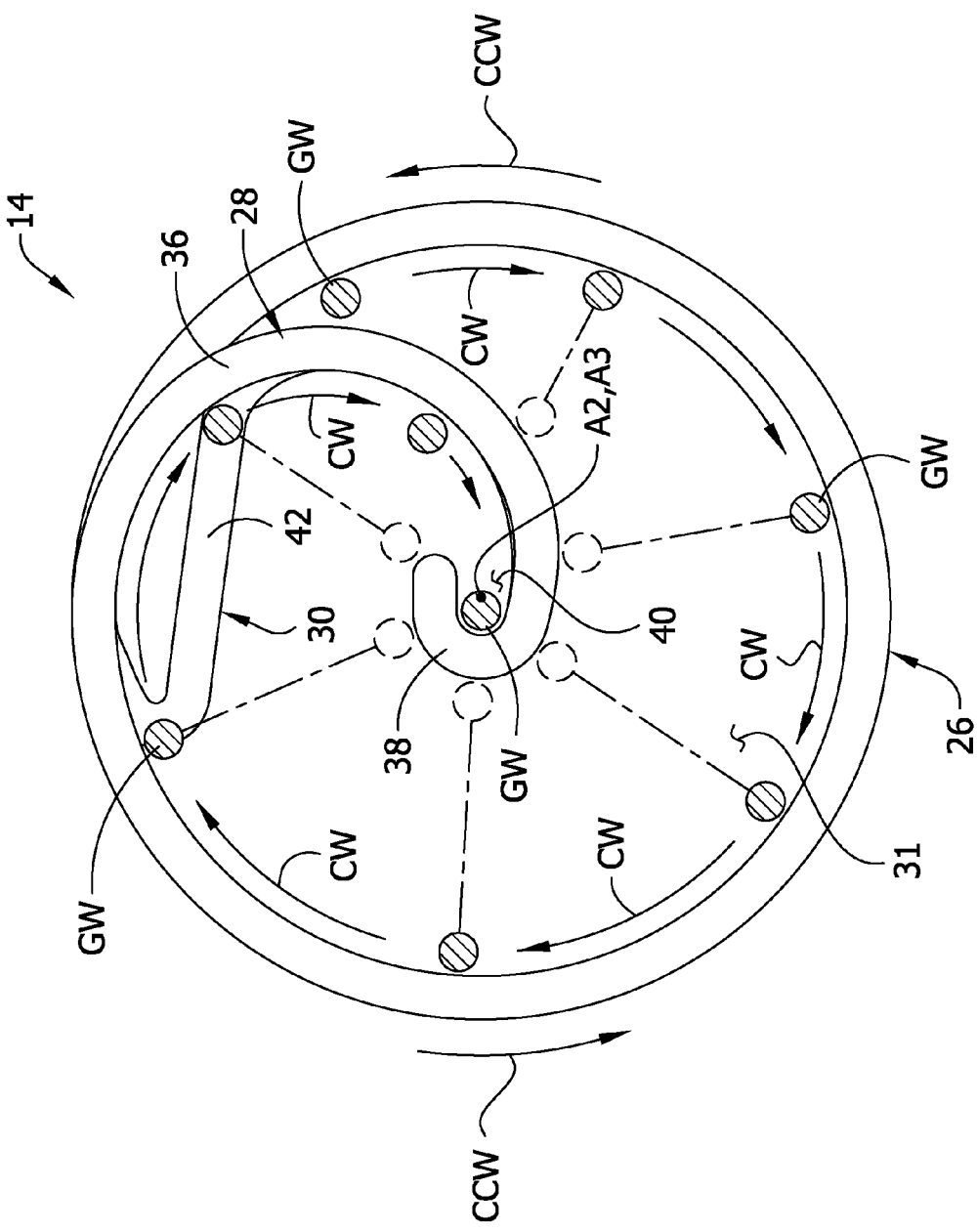
FIG. 4 is a front elevation of the guidewire capture device, showing a cross section of the guidewire in different angular positions in the guidewire capture device as the guidewire capture device is rotated about its axis.

Referring to FIG. 4, the hoop member 26 defines a hoop passage 31 and an outer dimension (or outer footprint as viewed from an end of the guidewire capture device 14) of the guidewire capture device. In the illustrated embodiment, the perimeter of the hoop member 26 extends a full 360 degrees about the axis A2 of the guidewire capture device 14. When inserted into the body lumen and in its expanded configuration, the hoop member 26 may be configured to engage the body lumen wall about its full 360 degree perimeter and generally conform to the cross-sectional size and shape of the body lumen. In this way, any radial gaps between the hoop member 26 and the wall of the body lumen are minimized to ensure the retrograde guidewire enters the hoop member, as explained in more detail below. In the illustrated embodiment, the guidewire capture device 14 has a generally circular footprint in its expanded configuration, whereby the radius of curvature of the footprint is generally constant about its perimeter. The footprint of the guidewire capture device 14 as defined by the hoop member 26 may have other shapes, such as oval or rectilinear, among others, without departing from the scope of the present invention.

Referring to FIGS. 2 and 4, each of the first and second hook members 28, 30 includes a curved shank 36 extending inwardly from the hoop member generally toward the axis A2 of the guidewire capture device 14, and a bent end 38 (e.g., a bent free end) adjacent the axis A2 of the guidewire capture device that is bent or curved back toward the curved shank. In the illustrated embodiment, each of the curved shanks 36 has a generally spiral shape with a radius of curvature that tapers or decreases from adjacent the hoop member 26 toward the corresponding bent end 38. The curved shanks 36 and bent ends 38 of the first and second hook members 28, 30 have substantially the same arc-shaped footprint, as shown in FIG. 4. As shown in FIG. 4, each bent end 38 defines a capture channel 40 for receiving and capturing the retrograde guidewire, as explained in more detail below. The capture channel has a channel axis A3 that is generally coaxial with the axis Al of the guidewire retrieval lumen (i.e., the channel axis A3 is aligned with the guidewire retrieval lumen).

In the illustrated embodiment, the guidewire capture device 14 is formed as a unitary, one-piece construction. For example, the guidewire capture device 14 may be formed from a wire or other elongate structure. The hoop member 26 includes a coiled body including a turn (e.g., a single turn) having proximal and distal ends. The first hook 28 is contiguous with a distal end of the coiled body of the hook member 26 (thereby constituting a distal hook), and the second hook 30 is contiguous with a proximal end of the coiled body (thereby constituting a proximal hook). The distal hook 28 projects distally outward from the coiled body of the hook member 26, as shown in FIG. 2, while the proximal hook 30 projects proximally outward from the coiled body. The proximal hook 30 includes a transition section 42 (FIG. 4) connecting the corresponding curved shank 36 to the proximal end of the hoop member 26. The guidewire capture device 14 also includes a proximal shaft 44 (FIGS. 2 and 3) contiguous with and extending proximally from the proximal hook member 30, in particular the bent end 38 of the proximal hook member. As shown in FIG. 2, the proximal shaft 44 is received in the guidewire retrieval lumen 18 and secured to the retrieval catheter 12, such as by adhesion, welding, overmolding, fasteners, or in other ways.

In the illustrated embodiment, the retrieval catheter 12 may be configured to transfer torque along its length, from its proximal end portion 12a to its distal end portion 12b, and impart rotation to the guidewire capture device 14 about its axis A2. For example, the retrieval catheter 12 may include the torque tube 20 (e.g., a metal coil; FIG. 1) for transferring torque alone its length. In this example, torque may be applied to the proximal end portion 12a of the retrieval catheter 12 that is outside the body of the subject, whereby the guidewire capture device 14 rotates with the retrieval catheter 12 about its axis A2. In other embodiments, the guidewire capture device 14 may be rotatable about its axis A2 independent of the retrieval catheter 12. In such an embodiment, a torque shaft (i.e., a shaft capable of transmitting torque along its length; not shown) may be connected to the proximal shaft 44, or some other component and/or structure, of the guidewire capture device 14. The torque shaft may extend along the length of the retrieval catheter 12 and through the proximal end portion of the retrieval catheter so that a proximal end portion of the torque shaft is accessible outside the subject's body. In this embodiment, torque applied to the proximal end portion of the torque shaft imparts rotation to the guidewire capture device 14 about its axis A2 such that the guidewire capture device rotates independent of and relative to the retrieval catheter 12.

Referring to FIG. 4, rotation of the guidewire capture device 14 about its axis A2 (such as in a counterclockwise direction as indicated by arrows CCW) moves at least one of the hook members 28, 30 into engagement with a retrograde guidewire GW that is received within the hoop member 26. As the guidewire capture device 14 continues to rotate, the retrograde guidewire GW moves along the curved shank(s) 36 and enters the capture channel 40, whereupon the guidewire is captured and generally aligned with the guidewire retrieval lumen 18. FIG. 4 also shows movement of the retrograde guidewire GW from the perspective of the capture device 14. From this perspective, the retrograde guidewire moves in a clockwise direction relative to the guidewire capture device 14, as indicated by arrows CW. The retrograde guidewire GW will be picked up and captured by at least one of the hook members 28, 30 regardless of the position of the guidewire in the hoop member 26. That is, as long as the retrograde guidewire GW is within the hoop member 26, at least one of the hook members 28, 30 will pick up and capture the guidewire so that the guidewire is generally aligned with the guidewire retrieval lumen.

Figure 5:
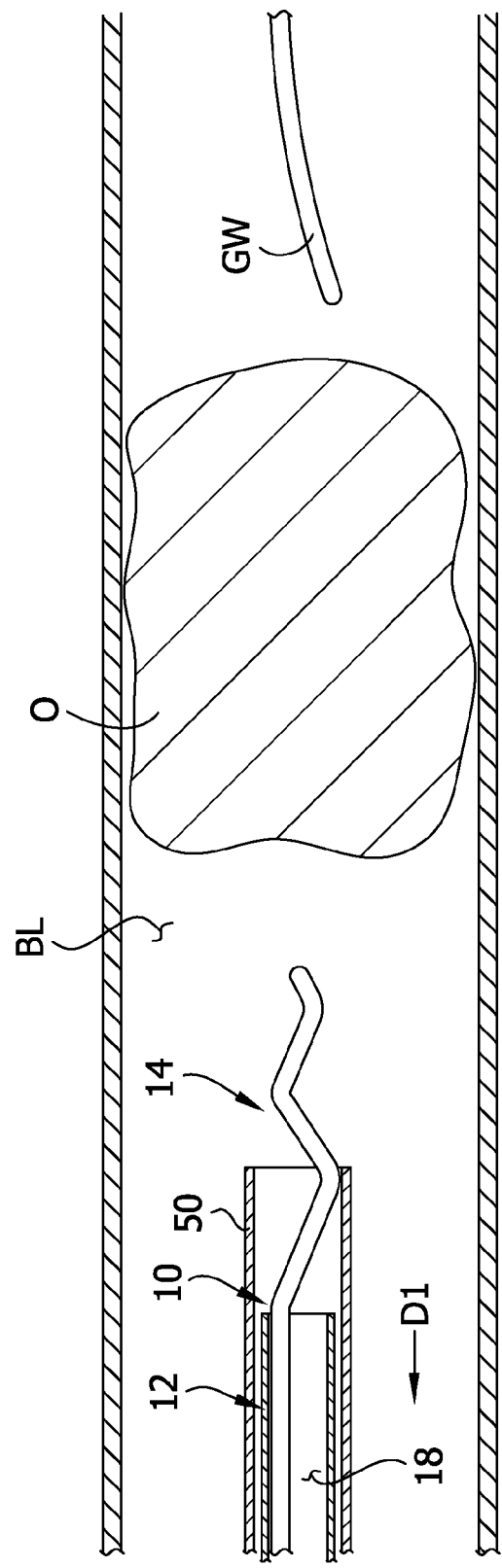
FIG. 5 is a schematic, partial longitudinal section illustrating the guidewire retrieval system being introduced into an occluded body lumen, the guidewire capture device being in a collapsed configuration.

An exemplary method of retrieving the retrograde guidewire GW from a body lumen will now be described. Referring to FIG. 5, the retrograde guidewire GW is introduced into a body lumen BL at a first side (e.g., a distal side) of an occlusion O of the body lumen, and the guidewire retrieval system 10 is introduced into the body lumen at a second side (e.g., a proximal side) of the occlusion. For example, where the body lumen BL is a peripheral artery in a leg of a subject, the retrograde guidewire GW may be inserted into the artery at an inferior location so that the guidewire approaches a distal cap of the occlusion O, and the guidewire retrieval system 10 may be inserted into the artery at a superior location so that the guidewire retrieval system approaches the proximal cap of the occlusion. In one example, the occlusion O may be a chronic total occlusion.

Figure 6:
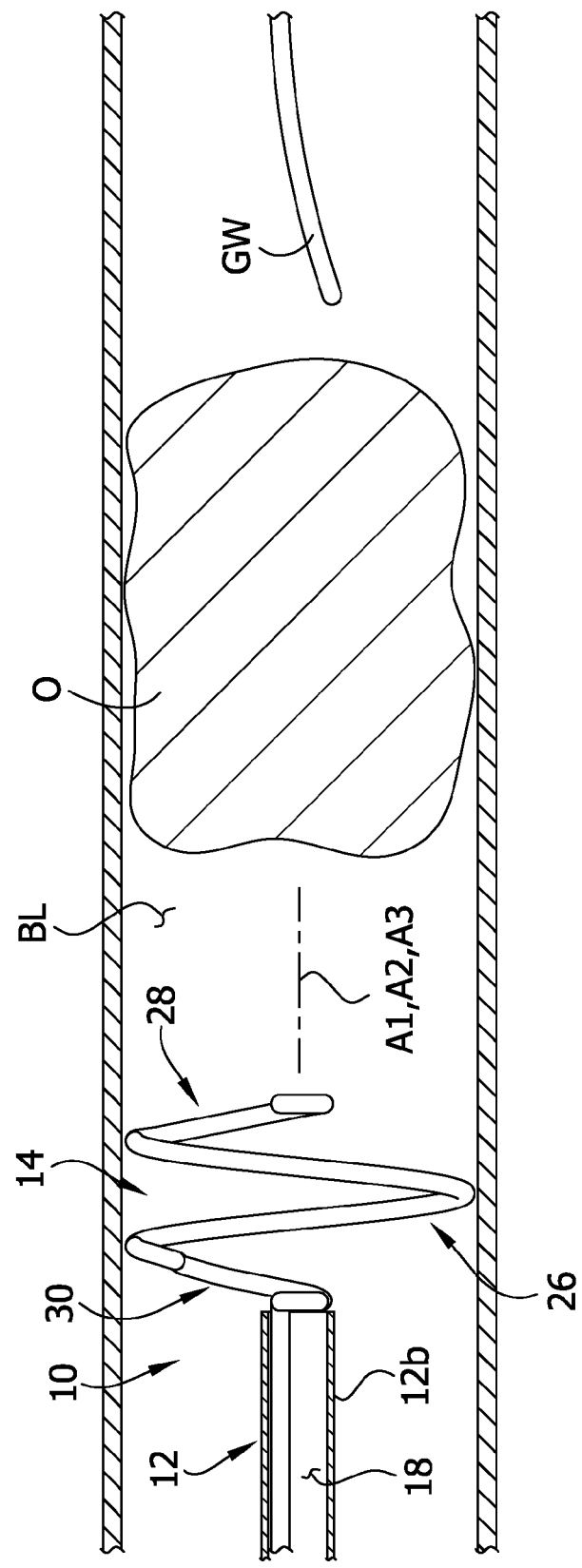
FIG. 6 is similar to FIG. 5, except the guidewire capture device is in an expanded configuration.

Referring still to FIG. 5, the guidewire retrieval system 10 may be inserted into the body lumen BL (e.g., a blood vessel) using an introducer sheath 50. In particular, the introducer sheath 50 may be delivered to a location adjacent the proximal cap of the occlusion O, and then the guidewire retrieval system 10 may be introduced into and fed along the introducer sheath to a distal end of the sheath. The introducer sheath 50 can then be withdrawn (e.g., pulled back in direction D1) from the body lumen BL leaving the guidewire capture device 14 of the guidewire retrieval system 10 adjacent the proximal cap of the occlusion O. As shown in FIG. 5, the guidewire retrieval system 10 is introduced into the body lumen with the guidewire capture device 14 in its collapsed configuration. As shown in FIG. 6, the guidewire capture device 14 assumes the expanded configuration after removal from the introducer sheath 50. As set forth above, in one example the guidewire capture device 14 may comprise shape memory material, such as nitinol, that assumes the expanded configuration when inserted into a body, or in another example the guidewire capture device may comprise a resilient material that rebounds to the expanded configuration after exiting the introducer sheath 50. Although FIGS. 5 and 6 show the guidewire retrieval system 10 being introduced and the guidewire capture device 14 being expanded before the retrograde guidewire GW has passed through the occlusion O, the guidewire retrieval system may be introduced after the guidewire has passed through the occlusion or at other times during the procedure to retrieve the retrograde guidewire. In another example, where the retrieval catheter 12 and the guidewire capture device 14 are separate components, as described above, the guidewire capture device may be received in the retrieval catheter in a collapsed configuration and then advanced through the distal end of the retrieval catheter where it assumes the expanded configuration.

Figure 7:
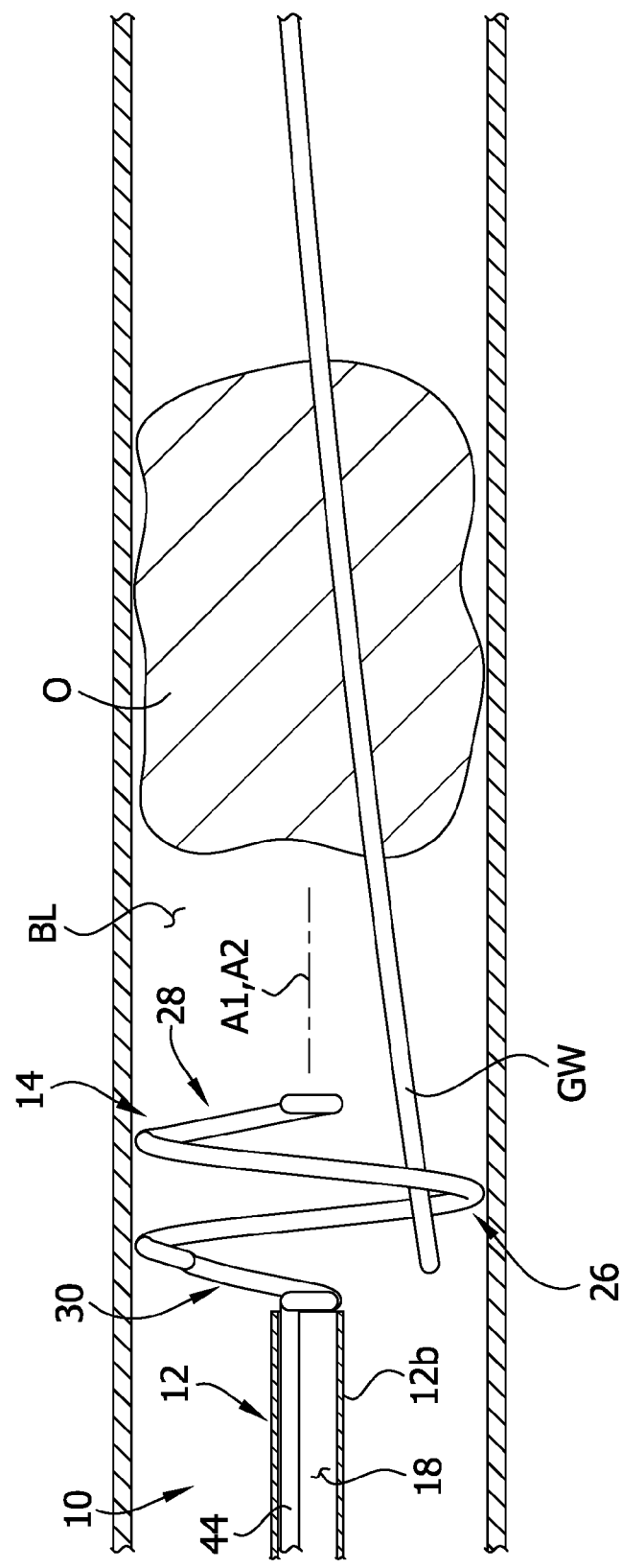
FIG. 7 is similar to FIG. 6, except a retrograde guidewire is being introduced into the guidewire capture device.
Figure 8:
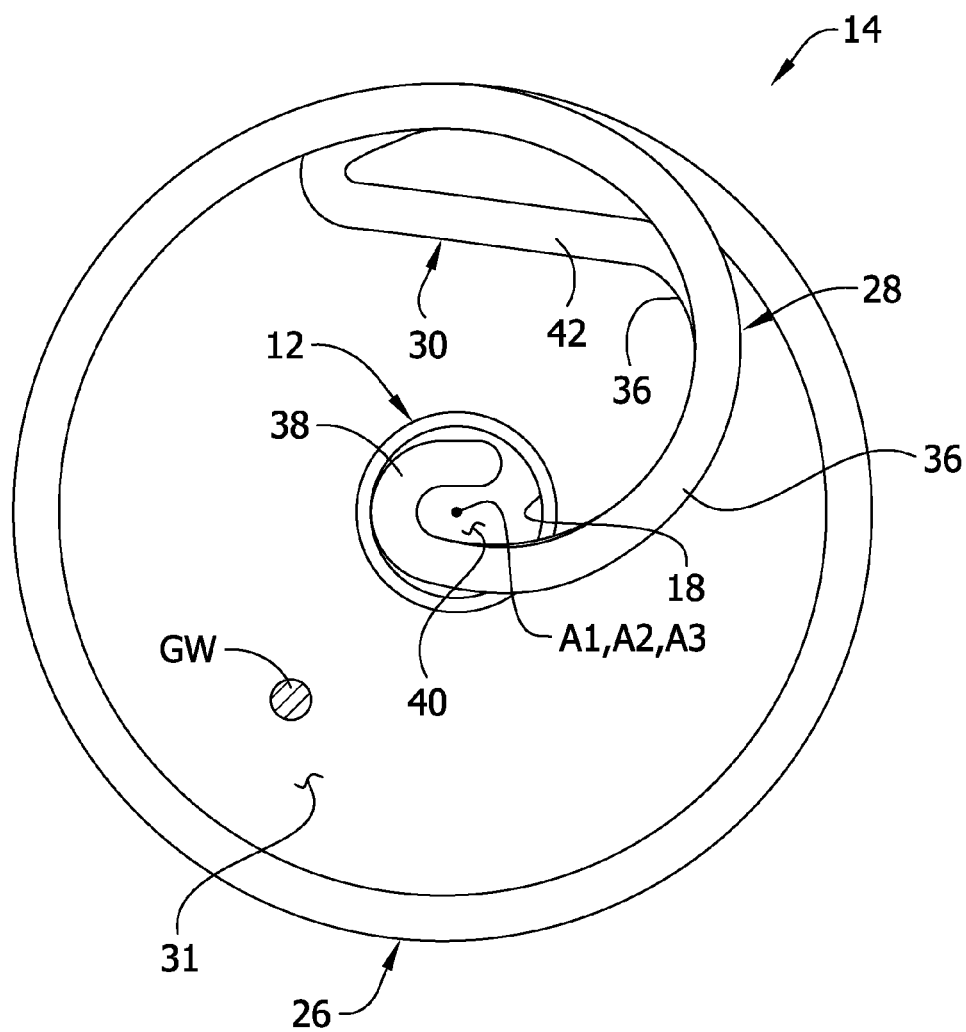
FIG. 8 is a front elevation of the guidewire retrieval system and a cross section of the retrograde guidewire as positioned in FIG. 7.

Referring to FIGS. 7 and 8, the retrograde guidewire GW is passed through the occlusion O from the distal cap through the proximal cap of the occlusion. After passing through the occlusion O, the tip portion of the retrograde guidewire GW is inserted into the hoop passage 31. In one example, the guidewire capture device 14 may be embedded, such as partially embedded, in the proximal cap of the occlusion to increase the likelihood of properly receiving the retrograde guidewire GW in the hoop passage 31. As can be seen from FIGS. 6 and 7, in its expanded configuration the hoop member 26 has a cross-sectional dimension suitable for engaging the wall of the body lumen BL around substantially a 360 degree circumference of the body lumen wall. The hoop member 26 may generally conform to the shape of the body lumen wall to minimize any gaps between the outer wall of the inflatable member and the body lumen wall. In this way, the hoop member 26 inhibits the retrograde guidewire GW from passing between the hoop member and the body lumen wall to facilitate insertion of the tip portion of the guidewire into the hoop passage 31.

The tip portion (i.e., the distal end portion) of the retrograde guidewire GW will typically be offset from the channel axis A3 after it passes through the occlusion O, and therefore, the guidewire will typically be positioned in the hoop passage 31 at a location offset from the channel axis. An example of retrograde guidewire GW entering the hoop passage 31 at a location offset from the channel axis A3 is shown in FIGS. 7 and 8. Confirmation that the retrograde guidewire GW has entered the hoop passage 31 may be made using imaging. For example, the tip portion of the retrograde guidewire GW may be radiopaque and the hoop member 26 and/or other portion(s) of the guidewire capture device 14 may be radiopaque to allow imaging of the relative positions of the guidewire tip portion and the hoop member. After the tip portion of the retrograde guidewire GW has entered the hoop member 26, the retrieval catheter 12 may be rotated about its axis A1 at its proximal end portion 12a, thereby imparting rotation to the guidewire capture device 14 about its axis A2.

Figure 9:
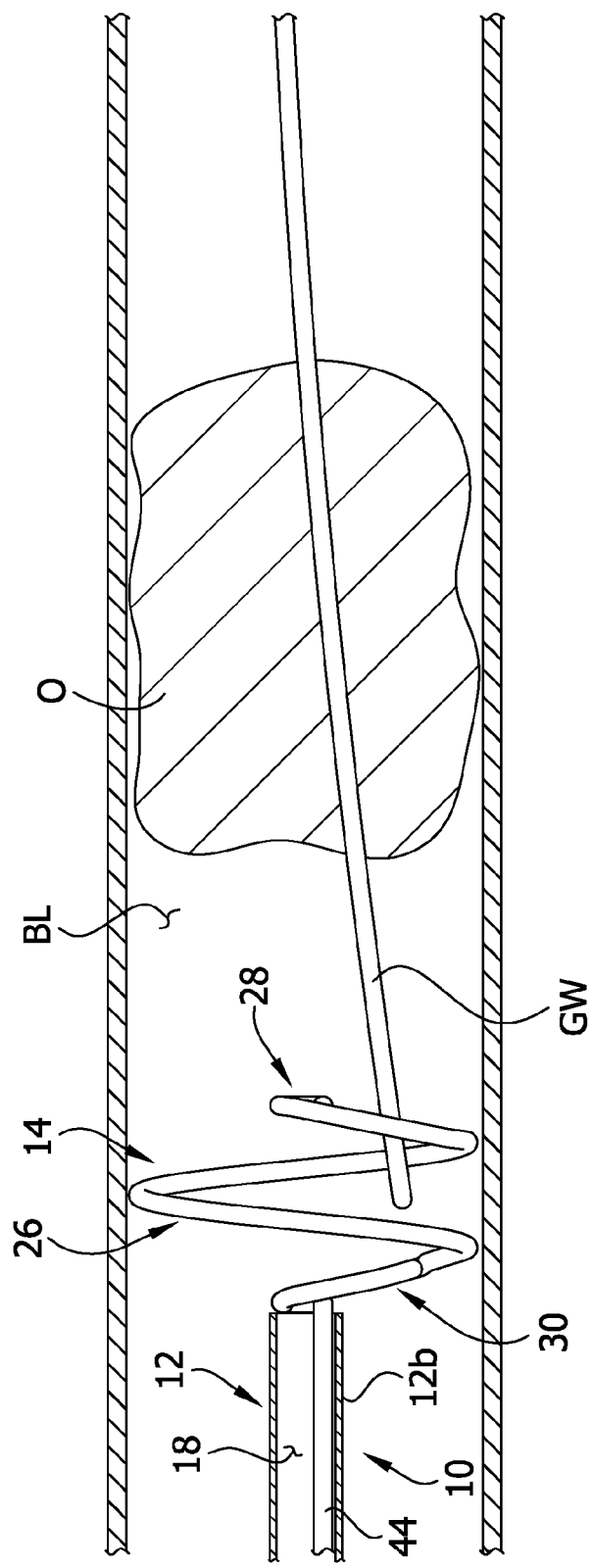
FIG. 9 is similar to FIG. 7, except the guidewire capture device is rotated about 180 degrees relative to its angular position in FIG. 7.
Figure 10:
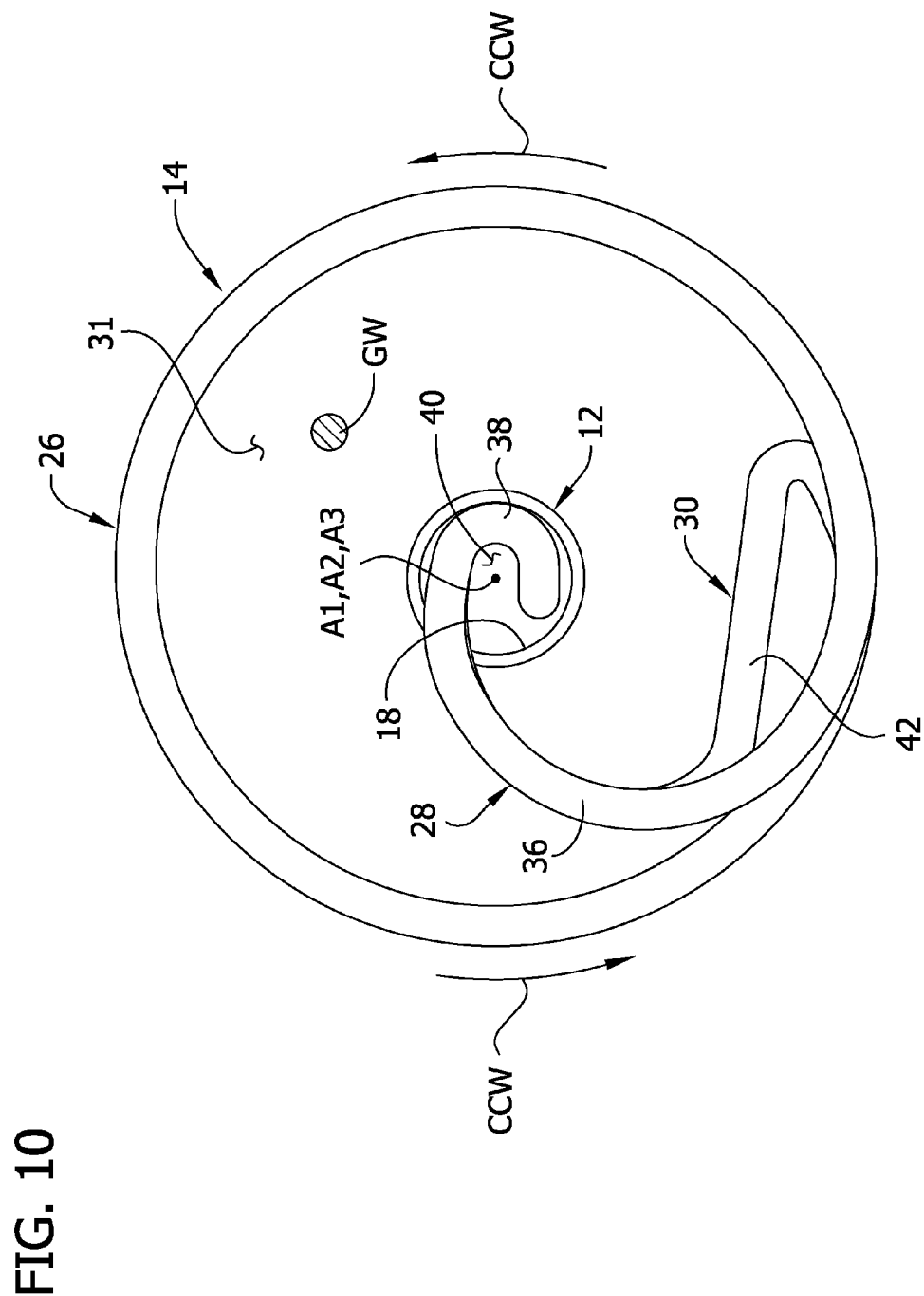
FIG. 10 is a front elevation of the guidewire retrieval system and a cross section of the retrograde guidewire as positioned in FIG. 9.
Figure 11:
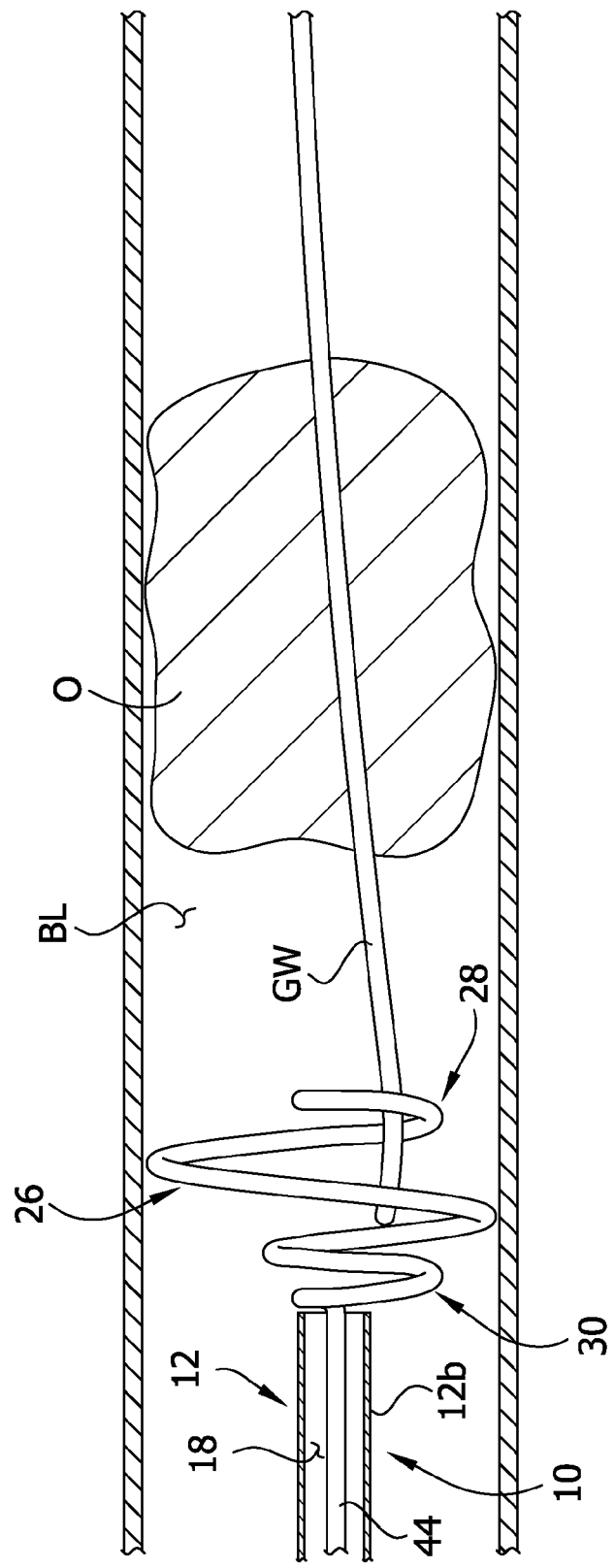
FIG. 11 is similar to FIG. 9, except the guidewire capture device is rotated about 270 degrees relative to its angular position in FIG. 7.
Figure 12:
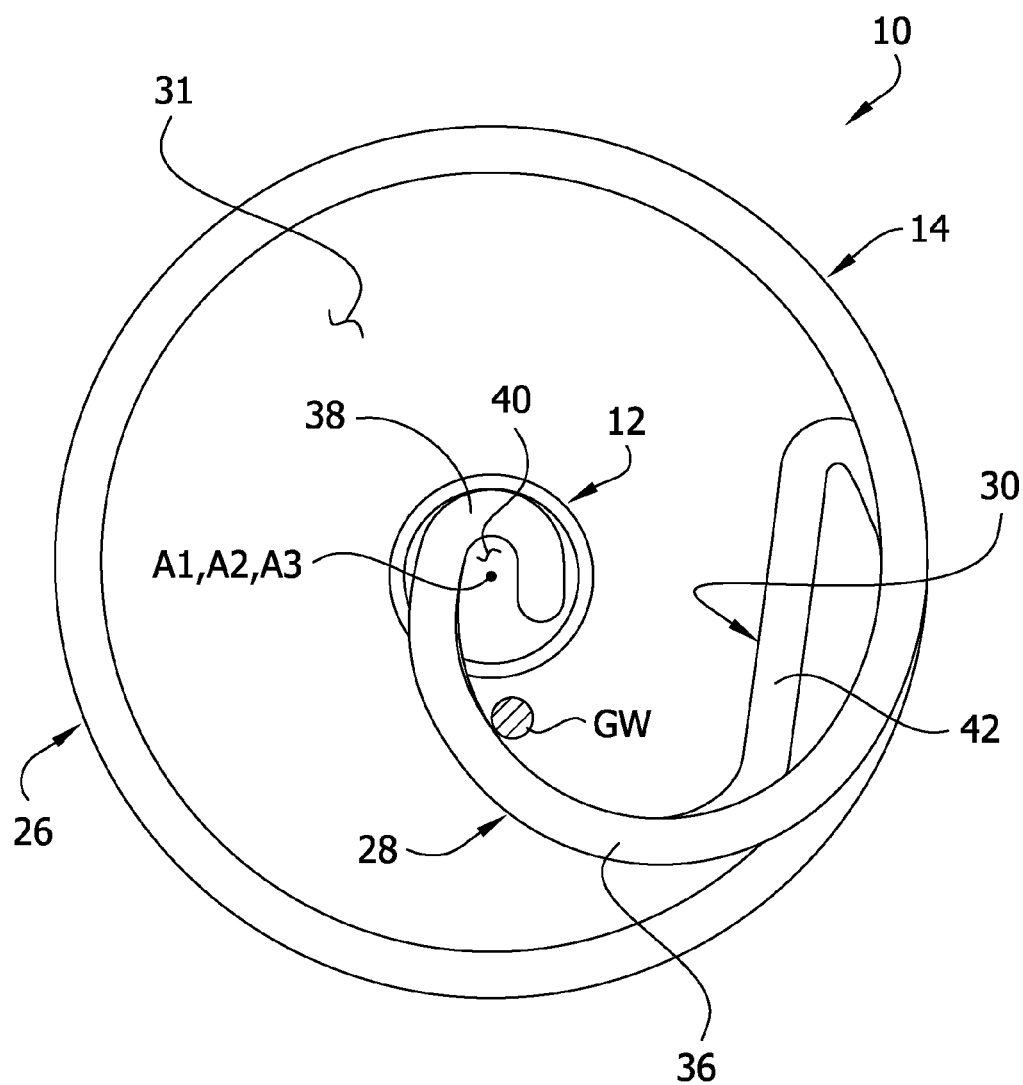
FIG. 12 is a front elevation of the guidewire retrieval system and a cross section of the retrograde guidewire as positioned in FIG. 11.
Figure 13:
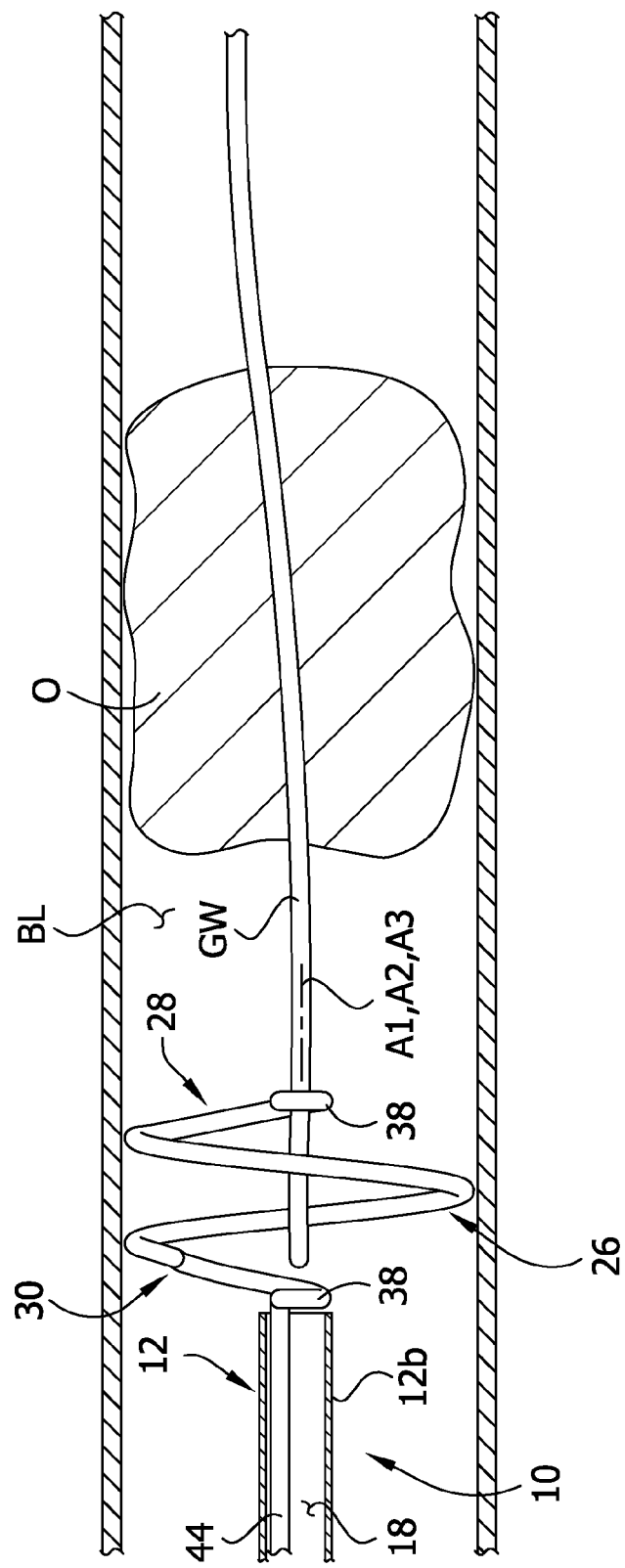
FIG. 13 is similar to FIG. 11, except the guidewire capture device is rotated about 360 degrees relative to its angular position in FIG. 7 and the guidewire is captured by the guidewire capture device.
Figure 14:
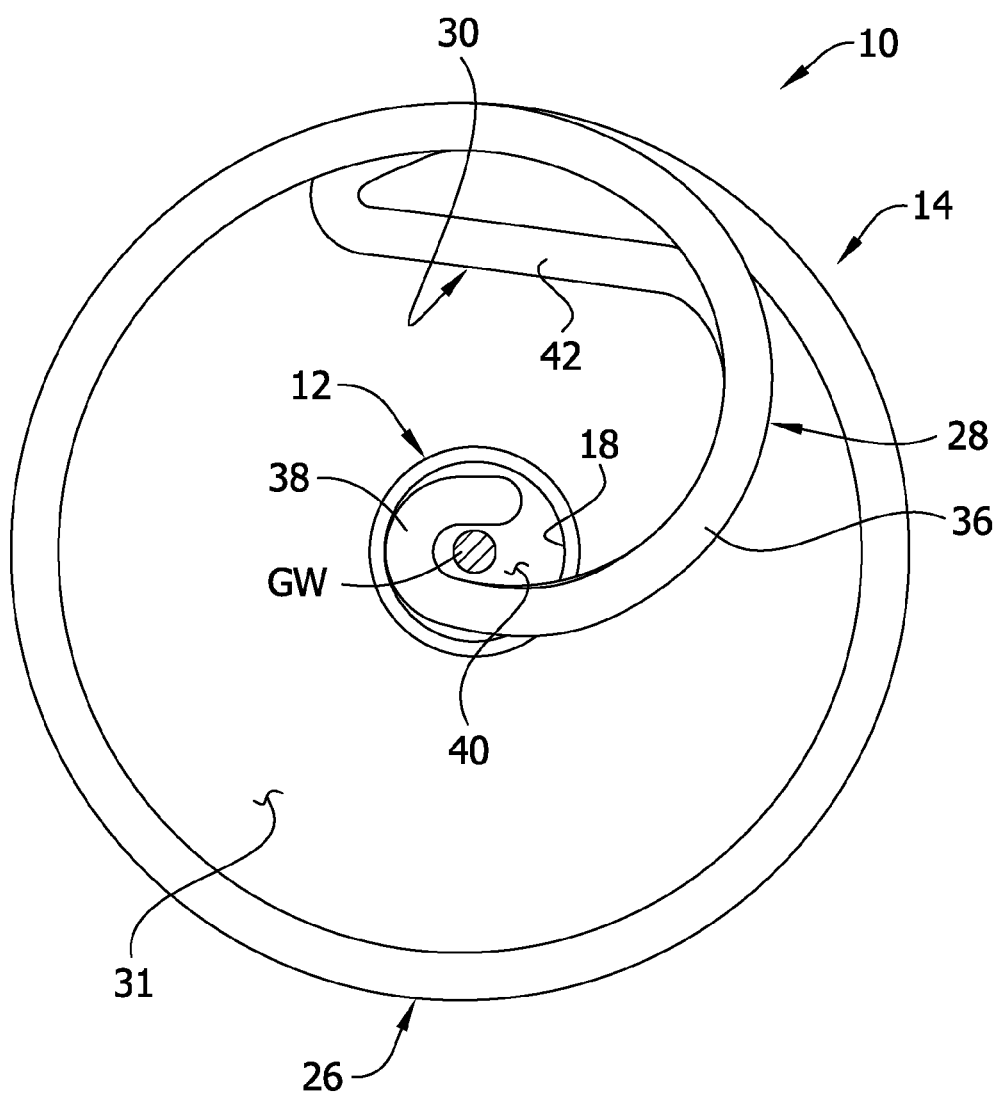
FIG. 14 is a front elevation of the guidewire retrieval system and a cross section of the retrograde guidewire as positioned in FIG. 13.

In the illustrated embodiment, the guidewire capture device 14 is rotated in a counterclockwise direction CCW, as viewed from the distal end of the device and shown in FIGS. 10, for example. For example, the proximal end portion of the retrieval catheter 12 may be rotated to impart rotation to the guidewire capture device 14 so that the retrieval catheter and the guidewire capture device rotate together. In another embodiment, a torque shaft (not shown) connected to the guidewire capture device 14 may be rotated to impart rotation of the guidewire capture device relative to the retrieval catheter 12. In the illustrated embodiment, the distal hook member 28, in particular the curved shank 36 of the distal hook member, engages the retrograde guidewire GW after about 180 degrees of rotation of the guidewire capture device 14 from its original angular position. The original angular position of the guidewire capture device is shown in FIGS. 7 and 8, and the angular position after 180 degrees of rotation about the axis A2 is shown in FIGS. 9 and 10. Continued rotation of the guidewire capture device 14 moves the retrograde guidewire GW along the curved shank 36 toward the capture channel 40. The angular position of the guidewire capture device 14 of the illustrated example after 270 degrees of rotation is shown in FIGS. 11 and 12. Continued rotation of the guidewire capture device 14 beyond about 270 degrees continues to move the retrograde guidewire GW along the curved shank 36 and into the capture channel 40. The angular position of the guidewire capture device 14 of the illustrated example after 360 degrees of rotation is shown in FIGS. 13 and 14. After about 360 degrees of rotation, the tip portion of the retrograde guidewire GW captured in the capture channel 40 of the distal hook member 28. It is understood that in other methods of use, the tip portion of the guidewire may be captured in the capture channels 40 of both the distal and proximal hook members 28, 30 during rotation of the guidewire capture device 14.

Figure 15:
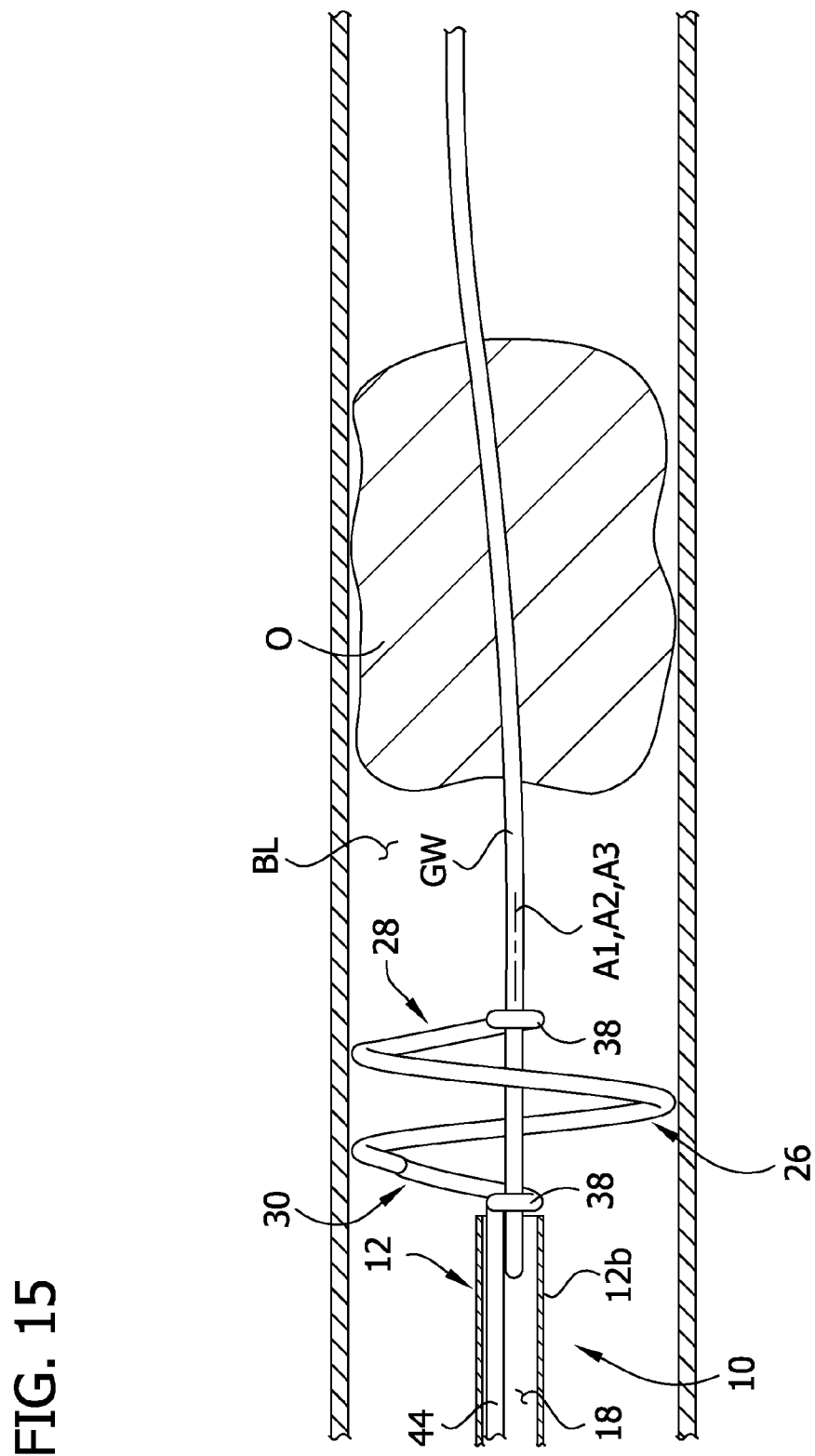
FIG. 15 is similar to FIG. 13, except the retrograde guidewire is received in a guidewire retrieval lumen of the guidewire retrieval catheter.

With the retrograde guidewire GW captured by the guidewire capture device 14 and aligned with the guidewire retrieval lumen 18, the guidewire can be advanced proximally into the guidewire retrieval lumen, such as by pushing the proximal end of the guidewire that is outside the subject's body. As shown in FIG. 13, the tip portion of the retrograde guidewire GW may be captured by only one of the hook members (e.g., the distal hook member 28) and spaced axially from the other hook member (e.g., the proximal hook member 30). However, as shown in FIGS. 13 and 15, because the capture channels 40 are axially aligned along the channel axis A3, the distal hook member 28 guides the tip portion of the guidwire GW into the channel of the proximal hook member 30, which further guides the tip portion of the guidewire into the guidewire retrieval lumen 18 as the guidewire is advanced proximally. The retrograde guidewire GW is fed through the guidewire retrieval lumen 18, in a proximal direction relative to the guidewire retrieval system 10, and exits the guidewire retrieval lumen (and the catheter 10) at a location outside the subject's body (not shown). With the tip portion of the retrograde guidewire GW disposed outside the subject's body, the guidewire retrieval system 10 can be removed from the body lumen BL. In particular, guidewire retrieval system 10 can be pulled back (e.g., moved proximally) into the distal end of the introducer sheath 50, thereby re-collapsing the guidewire capture device 14. Other ways of removing the guidewire retrieval system 10 do not depart from the scope of the present invention.

After removing the guidewire retrieval system 10, a medical device (e.g., a directional atherectomy device, a CTO crosser, a balloon catheter, etc.) can be inserted into the body lumen BL using the retrograde guidewire GW. The medical device can be fed along the retrograde guidewire GW to the proximal cap of the occlusion O to treat the occlusion. It is understood that the steps recited above may be modified, omitted, or performed any a different order for retrieving a retrograde guidewire in a body lumen.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A guidewire retrieval system for use in retrieving a guidewire from a body lumen, the guidewire retrieval system comprising:
   a retrieval catheter configured for insertion into the body lumen and having proximal and distal end portions, a length extending between the proximal and distal end portions, and a guidewire retrieval lumen extending lengthwise of the retrieval catheter for receiving the guidewire therein, the guidewire retrieval lumen having an axis;
   a guidewire capture device configured for insertion into the body lumen and having an axis about which the guidewire capture device is rotatable within the body lumen, the guidewire capture device including a hoop member defining a hoop passage for receiving the guidewire therein, and a hook member extending inwardly from the hoop member toward the axis of the guidewire capture device, wherein the hook member is configured to capture the guidewire received in the hoop passage as the guidewire capture device is rotated about its axis,
   wherein the hook member defines a capture channel configured to capture the guidewire, wherein the capture channel has a channel axis that is generally coaxial with the axis of the guidewire retrieval lumen such that the guidewire is aligned with the guidewire retrieval lumen when the guidewire is captured in the capture channel.

2. The guidewire retrieval system set forth in claim 1, wherein the guidewire capture device is configurable between a collapsed configuration, to facilitate insertion into the body lumen, and an expanded configuration, to facilitate insertion of the guidewire into the hoop passage.

3. The guidewire retrieval system set forth in claim 2, wherein the guidewire capture device comprises a unitary, one-piece construction formed from a single piece of material.

4. The guidewire retrieval system set forth in claim 3, wherein the guidewire capture device is formed from shape memory material.

5. The guidewire retrieval system set forth in claim 1, wherein the hook member includes a bent end generally adjacent the axis of the guidewire capture device, wherein the bent end defines the capture channel for capturing the guidewire and aligning the guidewire with the guidewire retrieval lumen.

6. The guidewire retrieval system set forth in claim 5, wherein the hook member includes a curved shank extending from the hoop member to the bent end for guiding the guidewire toward the capture channel as the guidewire capture device is rotated about its axis.

7. The guidewire retrieval system set forth in claim 6, wherein the hook member comprises two hook members, wherein the respective capture channels defined by the bent ends of the hook members define the channel axis that is generally coaxial with the guidewire retrieval lumen.

8. The guidewire retrieval system set forth in claim 1, wherein the guidewire capture device includes a shaft received in the guidewire retrieval lumen and secured to the retrieval catheter.

9. The guidewire retrieval system set forth in claim 1, wherein the retrieval catheter includes a torque tube for transmitting torque from the proximal end portion to the distal end portion of the retrieval catheter to impart rotation to the guidewire capture device.

10. The guidewire retrieval system set forth in claim 1, wherein the hoop member includes a coiled body having at least one 360 degree coiled tum extend around the axis of the guidewire capture device.

11. The guidewire retrieval system set forth in claim 10, wherein the hook member includes a proximal hook member extending from and contiguous with a proximal end of the coiled body of the hoop member.

12. The guidewire retrieval system set forth in claim 10, wherein the hook member includes a distal hook member extending from and contiguous with a distal end of the coiled body of the hoop member.

13. The guidewire retrieval system set forth in claim 12, wherein the hook member includes a proximal hook member extending from and contiguous with a proximal end of the coiled body of the hoop member.

14. The guidewire retrieval system set forth in claim 13, wherein each of the distal and proximal hook members includes a bent end defining the capture channel for receiving the guidewire therein.

15. The guidewire retrieval system set forth in claim 14, wherein each of the distal and proximal hook members includes a curved shank contiguous with and extending between the respective bent ends with the coiled body of the hoop member.

16. The guidewire retrieval system set forth in claim 1, wherein the hoop member is configured to engage and generally conform to a wall of the body lumen when in the expanded configuration.

17. A method of retrieving a guidewire from a body lumen, the method comprising:
   inserting a guidewire retrieval system into a body lumen of a subject, wherein the guidewire retrieval system includes a retrieval catheter having a guidewire retrieval lumen having an axis configured to receive a guidewire therein, and a guidewire capture device at a distal end of the catheter,
   expanding, after said inserting a guidewire retrieval system, the guidewire capture device such that after expansion the guidewire capture device includes a hoop member defining a hoop passage for receiving the guidewire therein, and a hook member extending inwardly from the hoop member toward an axis of the guidewire capture device, wherein the hook member defines a capture channel configured to capture the guidewire, wherein the capture channel has a channel axis that is generally coaxial with the axis of the guidewire retrieval lumen such that the guidewire is aligned with the guidewire retrieval lumen when the guidewire is captured in the capture channel.

18. The method of retrieving a guidewire from a body lumen set forth in claim 17, further comprising:
   inserting, after said expanding the guidewire capture device, a guidewire into the hoop passage; and
   rotating, after said inserting a guidewire into the hoop passage, the guidewire capture device about its axis, whereupon the guidewire enters and is captured by the capture channel so that the hook member aligns the guidewire with the guidewire retrieval lumen.

19. The method of retrieving a guidewire from a body lumen set forth in claim 18, further comprising:
   inserting, after said rotating the guidewire capture device about its axis, the distal end of the guidewire into the guidewire retrieval lumen of the retrieval catheter.

* * * * *